(12) United States Patent
Raey

(10) Patent No.: US 12,365,861 B2
(45) Date of Patent: Jul. 22, 2025

(54) INCUBATION MONITORING APPARATUS

(71) Applicant: Power to Innovate Technologies Inc., Burnaby (CA)

(72) Inventor: Ronald Vijay Dharam Raey, North Vancouver (CA)

(73) Assignee: Power to Innovate Technologies Inc., Burnaby (CA)

( * ) Notice: Subject to any disclaimer, the term of this patent is extended or adjusted under 35 U.S.C. 154(b) by 0 days.

(21) Appl. No.: 18/309,743

(22) Filed: Apr. 28, 2023

(65) Prior Publication Data

US 2024/0141279 A1 May 2, 2024

Related U.S. Application Data

(60) Provisional application No. 63/495,455, filed on Apr. 11, 2023, provisional application No. 63/381,691, filed on Oct. 31, 2022.

(51) Int. Cl.
| | | |
|---|---|---|
| *C12M 1/34* | (2006.01) | |
| *G01N 27/414* | (2006.01) | |
| *G01N 27/416* | (2006.01) | |
| *H04Q 9/00* | (2006.01) | |

(52) U.S. Cl.
CPC ........... *C12M 41/26* (2013.01); *G01N 27/414* (2013.01); *G01N 27/4167* (2013.01); *H04Q 9/00* (2013.01); *H04Q 2209/43* (2013.01); *H04Q 2209/88* (2013.01)

(58) Field of Classification Search
CPC . C12M 41/26; G01N 27/414; G01N 27/4167; H04Q 9/00; H04Q 9/43; H04Q 9/88
USPC ........................................................ 435/287.1
See application file for complete search history.

(56) References Cited

U.S. PATENT DOCUMENTS

2008/0318307 A1\* 12/2008 Spittle .................... C12M 41/26
 435/287.1
2020/0319217 A1\* 10/2020 Verhoef ................. C12M 1/005

\* cited by examiner

*Primary Examiner* — Michael L Hobbs
(74) *Attorney, Agent, or Firm* — Nixon Peabody LLP

(57) ABSTRACT

An embodiment of the invention concerns an apparatus for monitoring pH of a media in a chamber. The apparatus includes a housing with a top wall that defines a well configured to contain the media. The well has a bottom and at least one side that define a first aperture and a second aperture. A pH probe is located within the housing and includes a first electrode and a second electrode that are configured to measure the pH of the media. The first electrode extends through the first aperture to contact the media within the well. The second electrode extends through the second aperture to contact the media within the well. One or more circuit boards are located within the housing and are configured to receive data from the pH probe. The one or more circuit boards include a transmitter configured to transmit the data from the pH probe.

11 Claims, 5 Drawing Sheets

INCUBATION MONITORING APPARATUS

CROSS-REFERENCE TO RELATED APPLICATIONS

This application claims the benefit of, and priority to, U.S. Provisional Patent Application No. 63/495,455, filed on Apr. 11, 2023, and U.S. Provisional Patent Application No. 63/381,691, filed on Oct. 31, 2022, each of which is hereby incorporated by reference herein in its entirety.

TECHNICAL FIELD

This disclosure relates generally to monitoring apparatuses and systems and methods of using the same. More specifically, the disclosure is directed to apparatuses and systems and associated methods for monitoring a property or properties of a fluid, such as pH.

BACKGROUND

Incubation chambers are often used to temporarily house embryos and mimic a uterus environment to aid in the development of the embryos. Current embryo growth practices require unsealing incubation chambers on a regular basis to measure properties of fluid within the incubation chambers, such as pH, for embryonic growth control. Unsealing and resealing incubation chambers can have significant negative effects on the growth of the incubated embryos and the success rate of the embryonic fertilization process. Similar issues exist for monitoring the properties of fluids in discrete, sealed containers for other fields outside of incubation chambers.

Other current embryo growth practices utilize wired apparatuses to measure properties of fluid within the incubation chambers. Wired transmission of data by such apparatuses presents disadvantages, such as carbon dioxide, humidity, and oxygen leaks from the incubation chambers due to the incubation chambers being unable to seal properly based on the presence of the wire. Such leaks can negatively affect the embryonic growth process and the viability of the embryos in the incubation apparatus.

Thus, there is a need for wireless monitoring apparatuses and systems and methods of using the same that are capable of monitoring a property or properties of a fluid, such as pH, without regular unsealing and resealing of chambers containing the fluid, such as incubation chambers.

SUMMARY

An embodiment of the invention concerns an apparatus for monitoring pH of a media in a chamber. The apparatus includes a housing. The housing has a top wall, a bottom wall, and at least one sidewall. The top wall defines a well configured to contain the media. The well has a bottom and at least one side. The bottom, the at least one side, or a combination thereof define a first aperture and a second aperture. A pH probe is located within the housing. The pH probe includes a first electrode and a second electrode that are configured to measure the pH of the media. The first electrode extends through the first aperture so that the first electrode contacts the media within the well. The second electrode extends through the second aperture so that the second electrode contacts the media within the well. One or more circuit boards are located within the housing. The one or more circuit boards are configured to receive data from the pH probe. The one or more circuit boards include a transmitter. The transmitter is configured to transmit radio waves through the chamber to transmit the data from the pH probe. A power source is located within the housing. The power source is configured to supply power to the pH probe and the one or more circuit boards.

An aspect of the embodiment includes the housing being impermeable to liquids. A further aspect of the embodiment includes the pH probe being an ion-sensitive field-effect transistor. An aspect of the embodiment includes the one or more circuit boards being configured to convert the data received from the pH probe into a reading that is in a form understandable to a human. An aspect of the embodiment includes at least one of the one or more circuit boards being connected to the pH probe via a wire. An aspect of the embodiment includes the media being an embryonic media. An aspect of the embodiment includes the power source being configured to be charged wirelessly. An aspect of the embodiment includes the power source being configured to supply energy to the pH probe for more than five days before needing to be recharged. An aspect of the embodiment includes the radio waves being ultra-high frequency radio waves. An aspect of the embodiment includes the radio waves being suitable for Bluetooth® network communication. An aspect of the embodiment includes the chamber being an incubation chamber. A further aspect of the embodiment includes a temperature sensor. A further aspect of the embodiment includes a carbon dioxide sensor. A further aspect of the embodiment includes an oxygen sensor. A further aspect of the embodiment includes a humidity sensor.

An embodiment of the invention concerns a system for measuring pH of a media in a chamber. The system includes a pH probe. The pH probe is configured to measure the pH of the media. A housing houses the pH probe, and the housing is configured to fit inside the chamber. One or more circuit boards are located within the housing. The one or more circuit boards are configured to receive data from the pH probe. The one or more circuit boards include a transmitter. The transmitter is configured to transmit radio waves through the chamber to transmit the data from the pH probe. A monitor is located outside of the chamber. The monitor includes a receiver. The receiver is configured to receive the radio waves from the transmitter to receive the data from the pH probe. A power source is located within the housing. The power source is configured to supply power to the pH probe and the one or more circuit boards.

An aspect of the embodiment includes the chamber being an incubation chamber. A further aspect of the embodiment includes the housing being inside the incubation chamber. An aspect of the embodiment includes the media being an embryonic media. An aspect of the embodiment includes the housing being impermeable to liquids. An aspect of the embodiment includes the pH probe being an ion-sensitive field-effect transistor. An aspect of the embodiment includes at least one of the one or more circuit boards being connected to the pH probe via a wire. An aspect of the embodiment includes the power source being configured to be charged wirelessly. An aspect of the embodiment includes the power source being configured to supply energy to the pH probe for more than five days before needing to be recharged. An aspect of the embodiment includes the radio waves being suitable for Bluetooth® network communication. An aspect of the embodiment includes a temperature sensor within the housing. An aspect of the embodiment includes a carbon dioxide sensor within the housing. An aspect of the embodiment includes an oxygen sensor within the housing. An aspect of the embodiment includes a humidity sensor within the housing. An aspect of the embodiment includes the monitor including a display. An aspect of the embodiment includes the monitor being configured to convert the data received from the pH probe into a reading that is in a form understandable to a human. An aspect of the embodiment includes the display being configured to display the reading that is in the form understandable to the human.

An embodiment of the invention concerns a method of measuring pH in an incubation chamber. The method comprises providing a pH probe and a first media in a first incubation chamber, providing a monitor located outside of the first incubation chamber, measuring first pH data of the first media with the pH probe, and wirelessly transmitting the first pH data of the first media to the monitor.

An aspect of the embodiment includes the first media being an embryonic media. An aspect of the embodiment includes the method further comprising providing one or more embryos in the first incubation chamber. An aspect of the embodiment includes the method further comprising providing a second incubation chamber and a second media, wherein the second incubation chamber encloses the second media. A further aspect of the embodiment includes the second media being an embryonic media. An aspect of the embodiment includes the method further comprising providing one or more embryos in the second incubation chamber. An aspect of the embodiment includes the first media and the second media being the same. An aspect of the embodiment includes the method further comprising establishing a wireless connection between the monitor and the pH probe. An aspect of the embodiment includes the wireless connection being via Bluetooth®. An aspect of the embodiment includes the method further comprising closing the first incubation chamber. An aspect of the embodiment includes the establishing occurring before closing the first incubation chamber. An aspect of the embodiment includes the establishing occurring after closing the first incubation chamber. An aspect of the embodiment includes the pH probe being an ion-sensitive field-effect transistor. An aspect of the embodiment includes the measuring occurring over at least one day. An aspect of the embodiment includes the measuring occurring over at least three days. An aspect of the embodiment includes the measuring occurring over at least five days. An aspect of the embodiment includes the method comprising converting the first pH data measured with the pH probe into a first reading that is in a form understandable to a human.

An embodiment of the invention concerns a system. The system comprises one or more incubation apparatuses. Each of the one or more incubation apparatuses includes one or more incubation chambers. A first pH apparatus is within a first incubation chamber of the one or more incubation chambers. The first pH apparatus includes a first housing defining a first well. The first well contains a first media. The first housing includes a first pH probe and a first transmitter. The first pH probe is configured to measure pH of the first media. The first transmitter is configured to transmit first radio waves through the first incubation chamber. A second pH apparatus is within a second incubation chamber of the one or more incubation chambers. The second pH apparatus includes a second housing. The second housing defines a second well. The second well contains a second media. The second housing includes a second pH probe and a second transmitter. The second pH probe is configured to measure pH of the second media. The second transmitter is configured to transmit second radio waves through the second incubation chamber. A first bridge is located outside of the one or more incubation apparatuses. The first bridge includes a first transceiver. The first transceiver is configured to receive at least the first radio waves from the first transmitter and is configured to transmit third radio waves. A smart device is located outside of the one or more incubation apparatuses. The smart device includes a receiver. The receiver is configured to receive the third radio waves from the first transceiver and is configured to provide the pH of the first media, the pH of the second media, or both, to a user.

An aspect of the embodiment includes the first incubation chamber and the second incubation chamber being in a first incubation apparatus of the one or more incubation apparatuses. An aspect of the embodiment includes the first transceiver being configured to receive the second radio waves from the second transmitter. An aspect of the embodiment includes the smart device being located in a different room than the first incubation apparatus. An aspect of the embodiment includes the first bridge being located in a same room as the first incubation apparatus. An aspect of the embodiment includes the first incubation chamber being in a first incubation apparatus of the one or more incubation apparatuses, and the second incubation chamber being in a second incubation apparatus of the one or more incubation apparatuses, different from the first incubation apparatus. An aspect of the embodiment includes the system further comprising a second bridge located outside of the one or more incubation apparatuses. The second bridge includes a second transceiver. The second transceiver is configured to receive the second radio waves from the second transmitter and is configured to transmit fourth radio waves. The receiver is configured to receive the fourth radio waves from the second transceiver to provide the pHs of the first media and the second media to the user. An aspect of the embodiment includes the receiver being configured to receive the third radio waves from the first bridge and the fourth radio waves from the second bridge. An aspect of the embodiment includes the smart device being located in a different room than the first incubation apparatus. An aspect of the embodiment includes the first bridge being located in a same room as the first incubation apparatus. An aspect of the embodiment includes the first incubation chamber being in a first incubation apparatus of the one or more incubation apparatuses, and the second incubation chamber being in a second incubation apparatus of the one or more incubation apparatuses, different from the first incubation apparatus. An aspect of the embodiment includes the system further comprising a second bridge located outside of the one or more incubation apparatuses. The second bridge includes a second transceiver. The second transceiver is configured to receive the second radio waves from the second transmitter and is configured to transmit fourth radio waves. The receiver is configured to receive the fourth radio waves from the second transceiver to provide the pHs of the first media and the second media to the user. An aspect of the embodiment includes the receiver being configured to receive the third radio waves from the first bridge and the fourth radio waves from the second bridge. An aspect of the embodiment includes the smart device being located in a different room than the first incubation apparatus and the second incubation apparatus. An aspect of the embodiment includes the first incubation apparatus being located in a different room than the second incubation apparatus. An aspect of the embodiment includes the first bridge being located in a same room as the first incubation apparatus, and the second bridge being located in a same room as the second incubation apparatus. An aspect of the embodiment includes the data communicated by the first radio waves and the second radio waves being based on a Bluetooth® protocol. An aspect of the embodiment includes the data communicated by the third radio waves being based on a Wi-Fi® protocol.

An embodiment of the invention concerns an apparatus for measuring pH of a sample. The apparatus comprises a housing. The housing has a top wall, a bottom wall, and at least one sidewall. The housing defines a first aperture and a second aperture. A pH probe is located within the housing. The pH probe includes a first electrode and a second electrode that are configured to measure the pH of the sample and generate pH data. The first electrode extends through the first aperture so that the first electrode contacts the sample. The second electrode extends through the second aperture so that the second electrode contacts the sample. One or more circuit boards are located within the housing. The one or more circuit boards are configured to receive the pH data from the pH probe. The one or more circuit boards include a transmitter. The transmitter is configured to wirelessly transmit the pH data to outside of the apparatus. A power source is located within the housing. The power source is configured to supply power to the pH probe and the one or more circuit boards.

An aspect of the embodiment includes the pH data being transmitted to outside of the apparatus based on a Bluetooth® communication. An aspect of the embodiment includes the power source being configured to supply power to the pH probe for one day before needing to be recharged. An aspect of the embodiment includes the power source being configured to supply power to the pH probe for three days before needing to be recharged. An aspect of the embodiment includes the power source being configured to supply power to the pH probe for five days before needing to be recharged. An aspect of the embodiment includes the power source being configured to be recharged wirelessly. An aspect of the embodiment includes the pH probe being configured to measure the pH of the sample at predetermined time intervals. An aspect of the embodiment includes the pH probe being configured to monitor the pH of the sample over a period of time. An aspect of the embodiment includes the period of time being at least one day. An aspect of the embodiment includes the period of time being at least three days. An aspect of the embodiment includes the period of time being at least five days. An aspect of the embodiment includes the pH probe being configured to measure the pH of the sample with an accuracy of +/−0.01 pH. An aspect of the embodiment includes the pH probe being an ion-sensitive field-effect transistor. An aspect of the embodiment includes a temperature sensor within the housing. An aspect of the embodiment includes a carbon dioxide sensor within the housing. An aspect of the embodiment includes an oxygen sensor within the housing. An aspect of the embodiment includes a humidity sensor within the housing. An aspect of the embodiment includes the one or more circuit boards being configured to convert the pH data received from the pH probe into a reading that is in a form understandable to a human. An aspect of the embodiment includes one of the one or more circuit boards being connected to the pH probe via a wire. An aspect of the embodiment includes a length of the housing being less than 70 mm. An aspect of the embodiment includes a width of the housing being less than 70 mm. An aspect of the embodiment includes a height of the housing being less than 15 mm. An aspect of the embodiment includes the housing defining a well. The well has a bottom and one or more sides. An aspect of the embodiment includes the first aperture being located within the well. An aspect of the embodiment includes the first aperture being located within the bottom of the well. An aspect of the embodiment includes the second aperture being located within the well. An aspect of the embodiment includes the second aperture being located within the one or more sides of the well.

It is to be understood that both the foregoing general description and the following detailed description are exemplary and explanatory only and are not restrictive of the invention as claimed.

BRIEF DESCRIPTION OF THE DRAWINGS

Disclosed herein are embodiments of apparatuses, systems, and methods pertaining to monitoring the property or properties of a fluid within a chamber, such as an incubation chamber. This description includes drawings, wherein.

Figure 1:
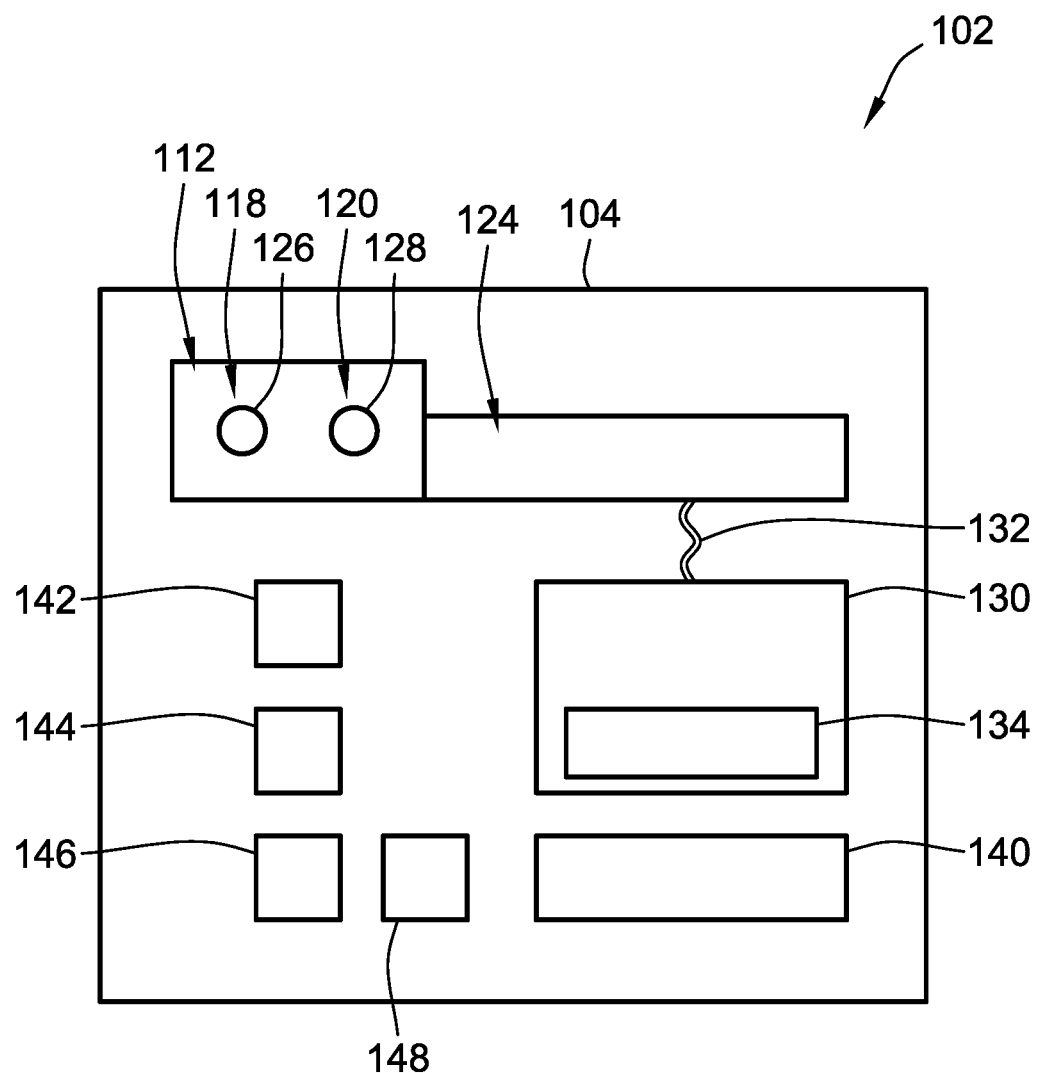
FIG. 1 shows a block diagram of an apparatus for monitoring a property or properties of a fluid, according to aspects of the present disclosure.

While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit of the invention as defined by the appended claims.

DETAILED DESCRIPTION

The present invention is described with reference to the attached figures, wherein like reference numerals are used throughout the figures to designate similar or equivalent elements. The figures are not drawn to scale, and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

Referring to FIG. 1, a block diagram of an apparatus 102 for monitoring a property or properties of a fluid, such as pH, is shown according to aspects of the present disclosure. The apparatus 102 includes a housing 104. The housing 104 houses various electronic components and sensors, described further below. The housing 104 can be made of any suitable material, including but not limited to metals, polymers, and ceramics. Suitable metals include titanium and titanium alloys, stainless steel, and cobalt-chromium alloy. Suitable polymers include medical-grade silicone, polyvinylchloride, polyethylene, polypropylene, polytetrafluoroethylene, acrylonitrile butadiene styrene (ABS), polyether ether ketone (PEEK), polymethylmethacrylate, trimethylcarbonate, and TMC NAD-lactide. Suitable ceramics include alumina, bioglass, hydroxyapatite, and zirconia. Regardless of the material used to form the housing 104, the housing 104 can be impermeable to liquids.

In some embodiments, the housing 104 has a length of about 70 mm or less. In some embodiments, the housing 104 has a width of about 70 mm or less. In some embodiments, the housing 104 has a height of about 15 mm or less. These dimensions allow for the apparatus 102 to fit within small chambers, as discussed further below.

The housing 104 defines a well 112 that is configured to hold a media. In some embodiments, the well 112 has a height and width of about 15 mm or less. In some embodiments, the well 112 has a depth of about 13 mm or less, such as about 10 mm. The well 112 can be any of a variety of suitable shapes. Some nonlimiting examples of suitable shapes include squares, rectangles, circles, ovals, hexagons, and octagons, all with either angled or rounded corners.

The well 112 defines a first aperture 118 and a second aperture 120. The first aperture 118 and the second aperture 120 are configured to allow various components within the housing 104 to contact media in the well 112, as discussed further below. The first and second apertures 118, 120 can be any of a variety of suitable shapes. Some nonlimiting examples of suitable shapes include squares, rectangles, circles, ovals, hexagons, and octagons, all with either angled or rounded corners.

A pH probe 124 is located within the housing 104 and includes a first electrode 126 and a second electrode 128. The first electrode 126 extends through the first aperture 118 so that the first electrode 126 can contact media in the well 112, as discussed further below. Similarly, the second electrode 128 extends through the second aperture 120 so that the second electrode 128 can contact the media in the well 112.

In some embodiments, the pH probe 124 is an ion-sensitive field-effect transistor (ISFET). In some embodiments, the pH probe 124 is a glass-free ISFET. In embodiments in which the pH probe 124 is an ISFET, the first and second electrodes 126, 128 include a pH electrode and a reference electrode that are used to pass a current through the media in the well 112. The current passed by the first and second electrodes 126, 128 changes as the ion concentrations (such as [H$^+$]) change in the media, and the changes in the current are used to measure the pH of the media. In other words, the difference in electric potential between the pH electrode, which is subject to change with different pH levels, and the reference electrode, which is not devised to change, provides a potentiometric measurement. This potentiometric measurement is then used to calculate the pH of the media.

The apparatus 102 further includes a circuit board 130 that is located within the housing 104. As shown in FIG. 1, the circuit board 130 is connected to the pH probe 124 via a connection 132. The circuit board 130 receives pH data from the pH probe 124 via the connection 132. In some embodiments, the connection 132 is a wire. In some embodiments, there are multiple circuit boards 130 within the housing 104. Examples of the circuit board 130 include a single layer PCB, double layer PCB, multi-layer PCB, rigid PCB, flex PCB, or rigid-flex PCB. In some embodiments, the circuit board 130 is configured to convert the data received from the pH probe 124 into a reading that a human would understand. For example, the circuit board 130 may use a mathematical formula to convert the pH data to a pH value between 0 and 14, according to a logarithmic pH scale.

The circuit board 130 includes a transmitter 134. The transmitter 134 transmits radio waves to transmit the pH data from the pH probe 124 to a monitor, as discussed further below. In some embodiments, the radio waves are ultra-high frequency radio waves. In some embodiments, the transmitter 134 transmits pH data based on a Bluetooth® communication by transmitting radio waves suitable for Bluetooth® network communication. The transmitter 134 is configured to transmit radio waves through the housing 104 to outside of the apparatus 102. The transmitter 134 is configured to transmit radio waves through a chamber that houses the apparatus 102. For example, the apparatus 102 may be located within an incubation chamber. The transmitter 134 is further configured to transmit the radio waves through the incubation chamber, including through any housing that holds the incubation chamber.

Transmitting radio waves through an apparatus, a housing, and/or an incubation chamber presents a challenge because radio waves encounter difficulty passing through electrical conductors, such as water or metals. Yet, many apparatuses or housings, such as incubation chambers, are made of various metals and electronic components that do not allow radio waves to pass through. Additionally, incubation chambers often have humidity levels of 85-95% to prevent evaporation of water from the media and to mimic the true ambient conditions that an embryo would grow. These high humidity levels present a further difficulty for transmitting radio waves. Radio wave transmission is also often interrupted by the insulation components of incubation chambers. Therefore, the transmitter 134 is small enough to fit within the apparatus 102 and also has a strong enough signal transmission to transmit radio waves through apparatuses or housings, and incubation chambers. To overcome these challenges, some embodiments locate the transmitter 134 on the circuit board 130 such that the transmitter 134 is isolated from possible interference with the circuit board 130 and/or any sensors in the apparatus 102, such as the pH probe 124. In some embodiments, the housing 104 is impermeable to liquids and is not easily opened to prevent moisture from entering the interior of the apparatus 102.

The apparatus 102 also includes a power source 140 within the housing 104. The power source 140 supplies power to the pH probe 124 and the circuit board 130. Examples of the power source 140 include an alkaline, nickel metal hydride, or lithium-ion cell, or a battery containing multiple of such cells. In some embodiments, the power source 140 is configured to be charged wirelessly. According to some embodiments, the power source 140 is configured to supply energy to the pH probe 124 for one day, for three days, for five days, or for more than five days before needing to be recharged. It is also contemplated that the power source 140 can be a single use battery.

According to some embodiments, the apparatus 102 can include additional sensors, such as a temperature sensor 142, a carbon dioxide sensor 144, an oxygen sensor 146, and/or a humidity sensor 148 located within the housing 104. In various embodiments, the apparatus 102 includes none of, one of, two of, three of, or all of the temperature sensor 142, the carbon dioxide sensor 144, the oxygen sensor 146, and the humidity sensor 148. Although only one temperature sensor 142 is shown in FIG. 1, in some embodiments there are multiple temperature sensors 142 such that one temperature sensor 142 can measure a temperature of a media in the well 112 and one temperature sensor can measure an ambient temperature. Having multiple temperature sensors 142 therefore provides valuable data regarding the time it takes for the media to approach the ambient temperature. It is also contemplated that the apparatus 102 includes a barometric pressure sensor. These additional sensors, in combination with the pH probe 124, can measure additional properties of the media within the well 112.

Figure 2:
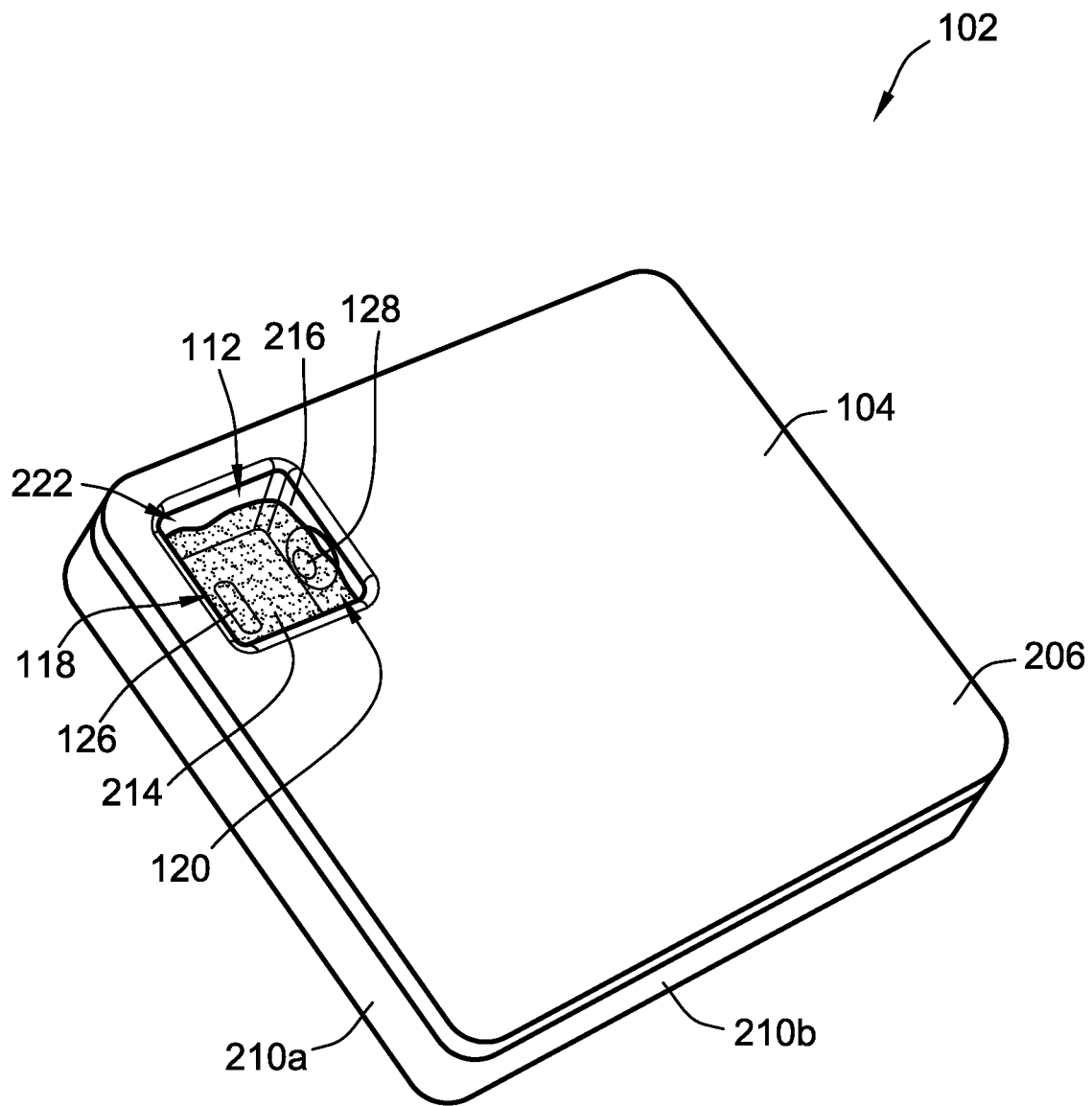
FIG. 2 shows a perspective view of the apparatus of FIG. 1, according to aspects of the present disclosure.

Now referring to FIG. 2, a perspective view of the apparatus 102 of FIG. 1 is shown, according to aspects of the present disclosure. The apparatus 102 includes the housing 104. The housing 104 has a top wall 206 and multiple sidewalls 210a, 210b. The top wall 206 defines the well 112 that is configured to contain a media 222. As discussed above, various properties of the media 222 can be monitored, such as pH, temperature, carbon dioxide concentration, oxygen concentration, humidity, or a combination thereof. In some embodiments, the media 222 is an embryonic media.

The well 112 has a bottom 214 and a sidewall 216. In some embodiments, the well 112 has multiple sidewalls 216. The bottom 214 can be any of a variety of suitable shapes. Some nonlimiting examples of shapes include a V-bottom, a U-bottom, an F-bottom, and a C-bottom.

The bottom 214 of the well 112 defines the first aperture 118. The first electrode 126 extends through the first aperture 118 so that the first electrode 126 contacts the media 222 in the well 112. Similarly, the sidewall 216 defines the second aperture 120. The second electrode 128 extends through the second aperture 120 so that the second electrode 128 contacts the media 222 in the well 112. Alternatively, the first electrode 126, the first aperture 118, the second electrode 128, and the second aperture 120 can be either both on the bottom 214 or both on one or more of the sidewalls 216.

Figure 3:
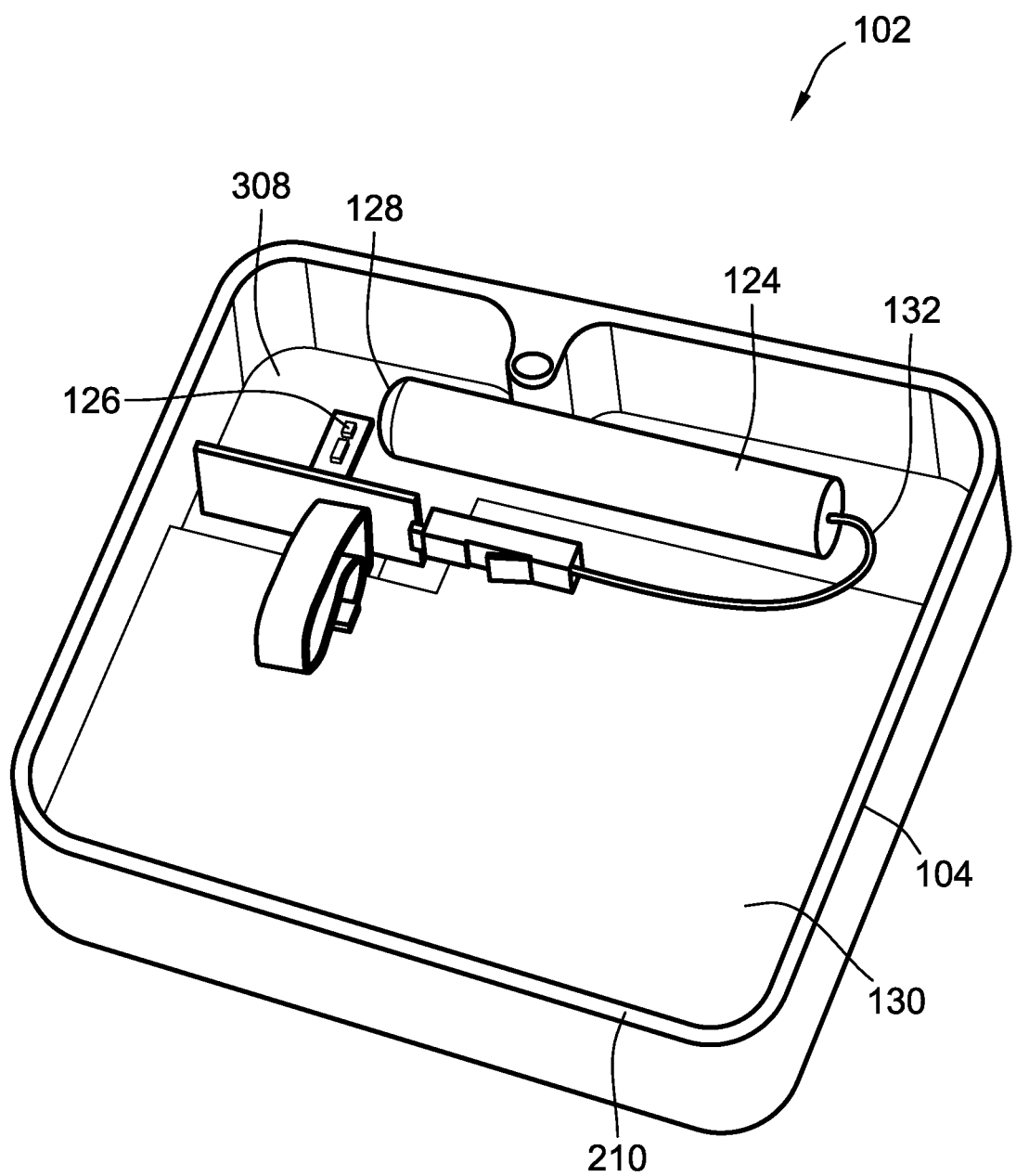
FIG. 3 shows an internal perspective view of the apparatus of FIGS. 1 and 2, according to aspects of the present disclosure.

Now referring to FIG. 3, an internal perspective view of the apparatus 102 of FIGS. 1 and 2 is shown, according to aspects of the present disclosure. The housing 104 has a bottom wall 308, which can connect to the pH probe 124. In some embodiments, the pH probe 124 is configured to monitor the pH of the sample over a period of time. In some embodiments, the period of time may be at least one day, at least three days, and/or at least five days. In some embodiments, the pH probe 124 is configured to measure the pH of the sample with an accuracy of +/−0.01 pH. In some embodiments, the apparatus 102 is configured to monitor the pH of the sample at fixed time intervals. A benefit of measuring characteristics of the sample at fixed intervals includes extending the period of time before the power source 140 needs to be recharged.

The apparatus 102 further includes the circuit board 130 configured to receive the pH data from the pH probe 124. The pH probe 124 is connected to the circuit board 130 via the connection 132 and receives pH data from the pH probe 124 via the connection 132. As shown in FIG. 3, the connection 132 is a wire. Although not shown in FIG. 3, the housing 104 includes the other components of the apparatus 102, as described above, such as the power source 140.

Figure 4:
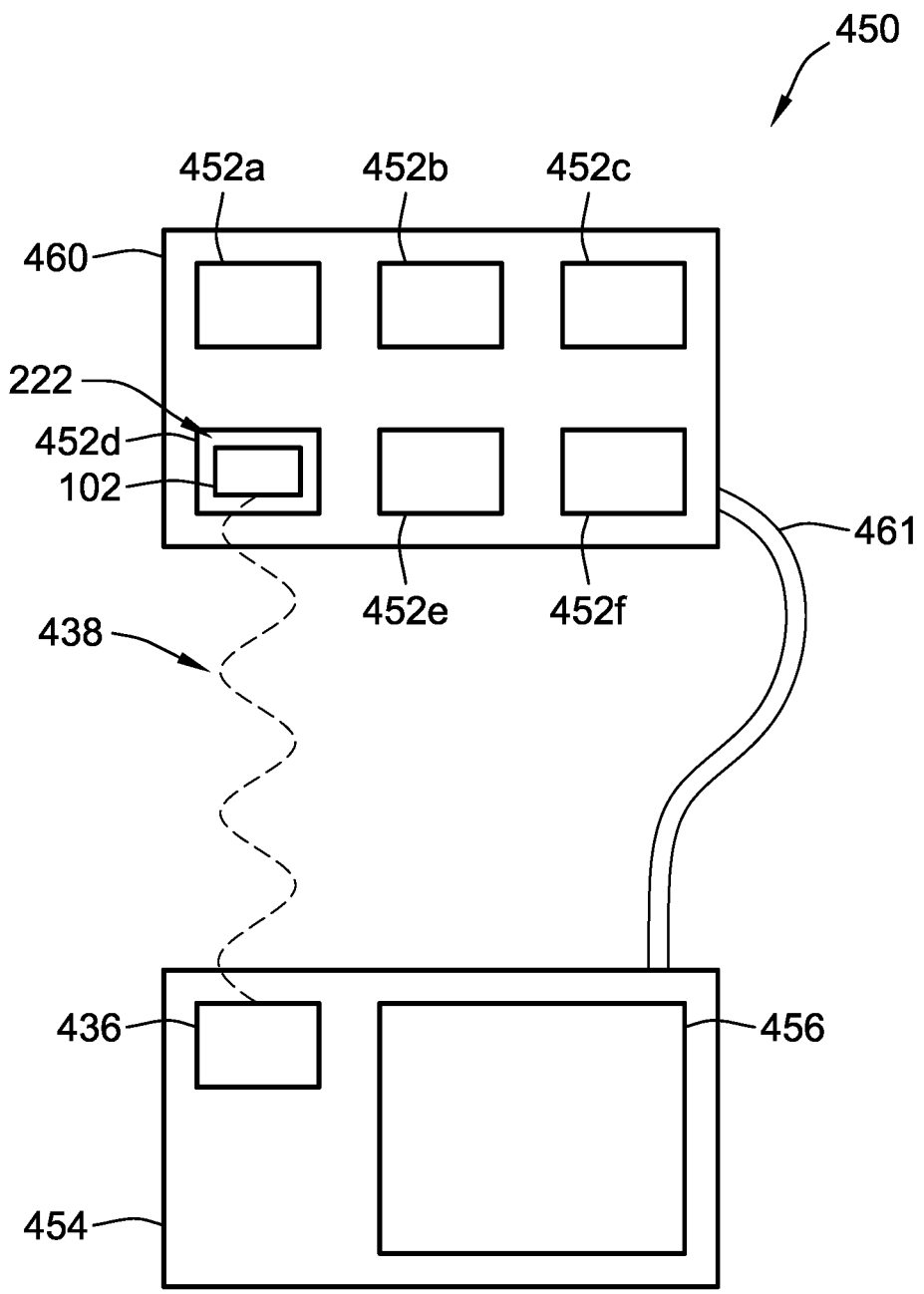
FIG. 4 shows a block diagram of a system for measuring a property or properties of a fluid, according to aspects of the present disclosure.

Now referring to FIG. 4, a block diagram of a system 450 for measuring a property or properties of a fluid, according to aspects of the present disclosure, is shown. The system 450 includes a chambered apparatus 460 and a monitor 454. The chambered apparatus 460 includes multiple chambers 452a, 452b, 452c, 452d, 452e, 452f. In some embodiments, the chambered apparatus 460 is an incubation apparatus and the chambers 452a, 452b, 452c, 452d, 452e, 452f are incubation chambers. In some embodiments, each chamber 452a, 452b, 452c, 452d, 452e, 452f of the chambered apparatus 460 contains an apparatus 102. In some embodiments, only some of the chambers 452a, 452b, 452c, 452d, 452e, 452f of the chambered apparatus 460 contains an apparatus 102, such as only the chamber of 452d.

As described above, media 222 is located within the well 112 of the apparatus 102, and the apparatus 102 is located within the chamber of 452d. The apparatus 102 measures various properties of the media 222, as described earlier herein, and transmits data describing the various properties of the media 222 via radio waves 438 to the monitor 454. In some embodiments, the radio waves 438 are ultra-high frequency radio waves. In some embodiments, the radio waves 438 are preferably suitable for Bluetooth® network communication. In some embodiments, the radio waves 438 are suitable for Wi-Fi® communication.

In some embodiments, the media 222 located within the well 112 of the apparatus 102 is the same media 222 being measured within each, or some of, the chambers 452a, 452b, 452c, 452d, 452e, 452f of the chambered apparatus 460. According to this arrangement, measurement of the properties of the media 222 in the chamber 452d by the apparatus 102 can be applied to all of the same media in the chambers 452a, 452b, 452c, 452d, 452e, 452f that contain the media. However, in some embodiments, the media 222 located within the well 112 of the apparatus 102 within each chamber 452a, 452b, 452c, 452d, 452e, 452f is different than the media 222 being measured in each or some of the chambers 452a, 452b, 452c, 452d, 452e, 452f of the chambered apparatus 460.

The monitor 454 is located outside of the chamber of 452d. In some embodiments, the monitor 454 is located outside of the chambered apparatus 460 that contains the chambers 452a, 452b, 452c, 452d, 452e, 452f. The monitor 454 includes a receiver 436 that is configured to receive the radio waves 438 from the apparatus 102. In some embodiments, the receiver 436 is located within the monitor 454 such that the receiver 436 is isolated from possible interference with various electronic components of the monitor 454.

In some embodiments, the monitor 454 is configured to convert the data received from the apparatus 102 into a reading that a human would understand. In some embodiments, the monitor 454 further includes a display 456, and the display 456 displays the reading that a human would understand. In some embodiments, the display 456 displays the current battery level of the apparatus 102, such as by a percentage or a status bar. It is contemplated that data may be downloaded from the monitor 454, such as via a USB stick or a wireless or wired connection to another device. In some embodiments, the monitor 454 includes an air tube 461 that connects to the chambered apparatus 460. The air tube 461 allows air in the chambered apparatus 460 to be pulled into the monitor 454 so that carbon dioxide and/or oxygen sensors within the monitor 454 can analyze carbon dioxide and/or oxygen content of the chambered apparatus 460. It is contemplated that the monitor 454 includes a memory to store the data received by the monitor 454.

A process of measuring pH in an incubation chamber, using the system 450 shown in FIG. 4, may be performed by different methods. One non-limiting example of a method of measuring pH in an incubation chamber includes providing the apparatus 102 loaded with the media 222 in the well 112 in the chamber 452d. For this example, the chamber 452d of FIG. 4 is an incubation chamber. The method further includes providing the monitor 454, located outside of the chamber 452d. The apparatus 102 measures the pH data of the media 222 via the pH probe 124 (not shown in FIG. 4). The pH data of the media 222 is then wirelessly transmitted to the monitor 454. The pH data is then converted into a reading that is in a form understandable to a human. In some methods, pH data is measured for at least one day, for at least three days, and/or for at least five days.

In some embodiments of the method, the media 222 is an embryonic media. In some embodiments, one or more embryos are placed in a different chamber 452e of the chambered apparatus 260. The embryo(s) are placed in the same media 222 as the media 222 in the well 112 of the apparatus 102 in the chamber of 452d. In some embodiments, the embryo(s) and the media 222 are in a petri dish within the chamber of 452e. By placing the same media 222 in the well 112 of the apparatus 102, and in the chamber 452e with the embryo(s), the pH of the media 222 in the chamber 452e with the embryo(s) can be approximated as being the same as the pH of the media 222 in the well 112. In such embodiments, the chamber 452e containing the embryo(s) does not need to be continuously unsealed and resealed to monitor the pH of the media 222. These embodiments therefore present advantages over current and past practices because unsealing and resealing incubation chambers throughout the embryonic growth process can have significant negative effects on the growth of the embryos and the success rate of the embryonic fertilization process.

In some methods of measuring pH in an incubation chamber, a wireless connection between the monitor 454 and the pH probe 124 is established via Bluetooth®. In some methods, the methods include closing the chamber 452d and/or the different chamber 452e. In some methods, the wireless connection is established prior to closing the chamber 452d and/or the different chamber 452e. In other methods, the wireless connection is established after closing the chamber 452d and/or the different chamber 452e. In some embodiments, some or all of the chambers 452a, 452b, 452c, 452d, 452e, 452f of the chambered apparatus 460 contain the apparatus 102, one or more embryos, or both. In some examples of the method, one or more embryos are provided in the same chamber 452d that contains the apparatus 102.

Figure 5:
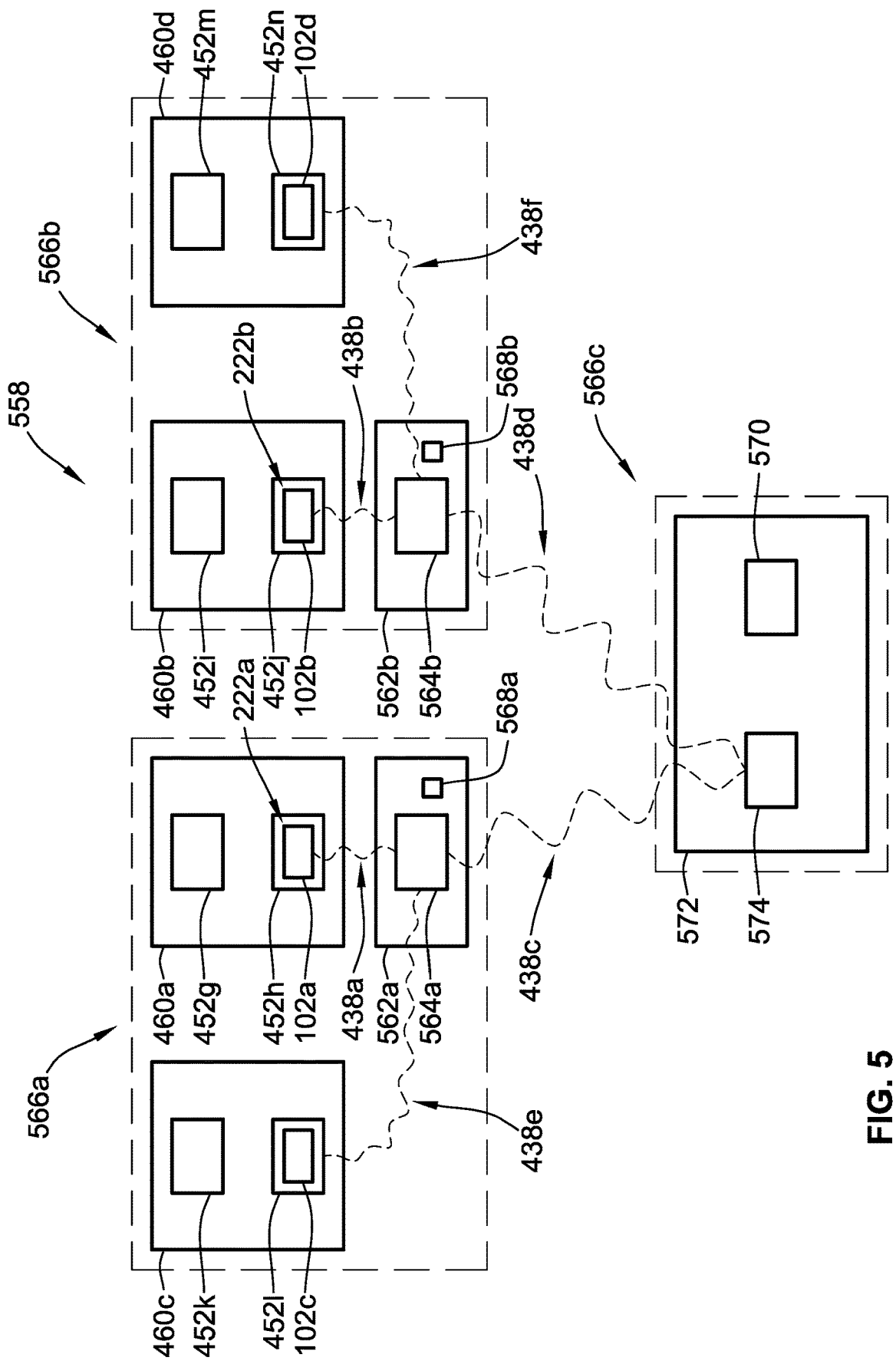
FIG. 5 shows a block diagram of a system for measuring a property or properties of fluids in different locations, according to aspects of the present disclosure.

FIG. 5 shows a schematic of a system 558 for measuring a property or properties of fluid in different locations, according to aspects of the present disclosure. The system 558 includes a first chambered apparatus 460a and a second chambered apparatus 460b. In some embodiments, the first chambered apparatus 460a and the second chambered apparatus 460b are incubation apparatuses. The apparatuses 460a, 460b each include multiple chambers 452g, 452h and 452i, 452j, respectively. In some embodiments, the chambers 452g, 452h, 452i, 452j are incubation chambers.

A first chamber 452h of the first chambered apparatus 460a holds a first apparatus 102a and a first media 222a within the well 112 of the first apparatus 102a. The first apparatus 102a is configured to measure the pH of the first media 222a and transmit first radio waves 438a through the first chamber 452h.

Similarly, a second chamber 452j of the second chambered apparatus 460b holds a second apparatus 102b and a second media 222b within the well 112 of the second apparatus 102b. The second apparatus 102b is configured to measure the pH of the second media 222b and transmit second radio waves 438b through the second chamber 452j. In some embodiments, the first radio waves 438a and the second radio waves 438b communicate data based on a Bluetooth® protocol. In some embodiments, the first chamber 452h and the second chamber 452j are both located in the first chambered apparatus 460a.

As shown in FIG. 5, the system 558 further includes a first bridge 562a located outside of the chambered apparatuses 460a, 460b, 460c, 460d. The first bridge 562a includes a first transceiver 564a that is configured to receive the first radio waves 438a from the first apparatus 102a and transmit third radio waves 438c. In some embodiments, the first transceiver 564a is configured to receive fifth radio waves 438e from a third apparatus 102c. The third apparatus 102c is in a third chambered apparatus 460c that has chambers 452k, 452l. In some embodiments, the first transceiver 564a is further configured to receive the second radio waves 438b from the second apparatus 102b (not shown in FIG. 5).

In some embodiments, the system 558 further includes a second bridge 562b located outside of the chambered apparatuses 460a, 460b, 460c, 460d. The second bridge 562b includes a second transceiver 564b configured to receive the second radio waves 438b from the second apparatus 102b and transmit fourth radio waves 438d. In some embodiments, the second bridge 562b is configured to receive sixth radio waves 438f from a fourth apparatus 102d. The fourth apparatus 102d is in a fourth chambered apparatus 460d that has chambers 452m, 452n. In some embodiments, data communicated by the third and fourth radio waves 438c, 438d is based on a Wi-Fi® protocol.

In some embodiments, the bridges 562a, 562b include a bridge display 568a, 568b. In some embodiments, the bridge displays 568a, 568b display data received via the first, second, fifth, and/or sixth radio waves 438a, 438b, 438e, 438f. In some embodiments, the bridges 562a, 562b are of a size that is easily transported, and as such, have bridge displays 568a, 568b that only display one type of data at a time, such as pH or temperature data. In further embodiments, the bridge displays 568a, 568b alternate the data shown at certain time intervals. For example, the bridge displays 568a, 568b may show pH data for five seconds, then alternate to show temperature data for five seconds, then alternate to show pH data for five seconds, and continue cycling through showing different types of data. In some embodiments, although not shown in FIG. 5, the bridges 562a, 562b include barometric pressure sensors.

The system 558 also includes the smart device 572 located outside of the chambered apparatuses 460a, 460b. The smart device 572 includes the receiver 574 that is configured to receive the third radio waves 438c and/or the fourth radio waves 438d. The smart device 572 and the receiver 574 are configured to provide the pH of the first media 222a and/or the second media 222b to a user, such as by displaying the pH on the display 570 of the smart device 572. In some embodiments, the smart device 572 includes a web application. In some embodiments, one or more of the bridges 56a, 562b are programmed to communicate with the smart device 572 via the web application. In some embodiments, the web application has graphical user interfaces that organize and display the data received via the third and/or fourth radio waves 438c, 438d on the display 570 of the smart device 572. In some embodiments, the smart device 572 is at a location remote from the bridges 562a, 562b.

In some embodiments, the first transceiver 564a is configured to receive first radio waves 438a from multiple chambers 452g, 452h of the first chambered apparatus 460a. Similarly, in some embodiments, the second transceiver is configured to receive second radio waves 438b from multiple chambers 452i, 452j of the second chambered apparatus 460b. The bridges 562a, 562b present advantages of being able to relay pH data over considerable distances from a plurality of chambers 452g, 452h, 452i, 452j. Further advantages of the bridges 562a, 562b include the ability to utilize both Bluetooth® and Wi-Fi® protocol. For example, establishing a connection between the apparatus 102 and the bridge 562a via Bluetooth® protocol may be easier than establishing a connection via Wi-Fi® protocol. Additionally, transmitting data via Wi-Fi® protocol allows data to be transmitted over greater distances than Bluetooth® protocol, so transmitting the third and fourth radio waves 438c, 438d via Wi-Fi® protocol enables the bridges 562a, 562b to communicate with devices, such as smart devices 472, that are too far away to communicate with via Bluetooth® protocol. In some embodiments, the transceivers 564a, 564b are located within the bridges 562a, 562b such that the transceivers 564a, 564b are isolated from possible interference with various electronic components of the bridges 562a, 562b.

In some embodiments, the smart device 572 is located in a different room 566c than a room 566a with the first chambered apparatus 460a. In some embodiments, the smart device 572 is located in a different room 566c than both the room 566a with the first and third chambered apparatuses 460a, 460c and a room 566b with the second and fourth chambered apparatuses 460b, 460d. In some embodiments, the first chambered apparatus 460a and the second chambered apparatus 460b are located in different rooms 566a, 566b. In some embodiments, the first bridge 562a is located in the same room 566a as the first chambered apparatus 460a. In some embodiments, the second bridge 562b is located in the same room 566b as the second chambered apparatus 460b. The bridges 562a, 562b present the advantage of being able to place the smart device 572 in a different room 566c, or even a different building, than the chambered apparatuses 460a, 460b. As such, only one smart device 572 is needed for displaying or obtaining pH data from a plurality of apparatuses 102 located within a plurality of chambered apparatuses 460a, 460b, 460c, 460d so that all of the pH data for a plurality of chambers 452g, 452h, 452i, 452j, 452k, 452l, 452m, 452n can be in one location.

In summary, the embodiments discussed above present a number of advantages over current and past embryonic growth practices. The wireless transmission of data accomplished by the apparatus 102 allows proper sealing of a corresponding chamber, such as a corresponding incubation chamber 452g-n. Further, the wireless transmission of data allows the user to measure properties of media in a chamber without the need to unseal and reseal the chamber every time a measurement is taken. Because the chamber 452 does not need to be unsealed and resealed for each measurement, the apparatus 102 is capable of continuously measuring various conditions of the media for a plurality of days. The use of monitors, bridges, and smart devices allows users to view data measured by the apparatus 102 from locations remote from the apparatus 102. This presents significant advantages, especially due to the increasing amount of work being done remotely.

Each of the above embodiments and obvious variations thereof are contemplated as falling within the spirit and scope of the claimed invention, which is set forth in the following claims. Moreover, the present concepts expressly include any and all combinations and sub-combinations of the preceding elements and aspects.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that the terms "exemplary" and "example" as used herein to describe various embodiments are intended to indicate that such embodiments are possible examples, representations, and/or illustrations of possible embodiments (and such terms are not intended to connote that such embodiments are necessarily extraordinary or superlative examples).

Any references herein to the positions of elements (e.g., "top," "bottom," "above," "below," etc.) are merely used to describe the orientation of various elements in the Figures. It should be noted that the orientation of various elements may differ according to other exemplary embodiments, and that such variations are intended to be encompassed by the present disclosure. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes, and omissions may also be made in the design, operating conditions, and arrangement of the various exemplary embodiments without departing from the scope of the present invention.

What is claimed is:
1. A system comprising:
two or more incubation apparatuses, each of the two or more incubation apparatuses including two or more incubation chambers;
a first pH apparatus within a first incubation chamber of a first incubation apparatus, the first pH apparatus including a first housing defining a first well, the first well containing a first media, the first housing including a first pH probe and a first transmitter, the first pH probe being configured to measure pH of the first media, the first transmitter being configured to transmit first radio waves through the first incubation chamber;
a second pH apparatus within a second incubation chamber of a second incubation apparatus, the second pH apparatus including a second housing defining a second well, the second well containing a second media, the second housing including a second pH probe and a second transmitter, the second pH probe being configured to measure pH of the second media, the second transmitter being configured to transmit second radio waves through the second incubation chamber;
a first bridge located outside of the two or more incubation apparatuses, the first bridge including a first transceiver, the first transceiver being configured to receive at least the first radio waves from the first transmitter and being configured to transmit third radio waves; and a smart device located outside of the two or more incubation apparatuses, the smart device including a receiver, the receiver being configured to receive the third radio waves from the first transceiver and being configured to provide the pH of the first media, the pH of the second media, or both, directly to a user.

2. The system of claim 1, wherein the first transceiver is configured to receive the second radio waves from the second transmitter.

3. The system of claim 1, wherein the smart device is located in a different room than the first incubation apparatus, and the first bridge is located in a same room as the first incubation apparatus.

4. The system of claim 1, further comprising: a second bridge located outside of the two or more incubation apparatuses, the second bridge including a second transceiver, the second transceiver being configured to receive the second radio waves from the second transmitter and being configured to transmit fourth radio waves, wherein the receiver is configured to receive the fourth radio waves from the second transceiver to provide the pHs of the first media and the second media to the user.

5. The system of claim 4, wherein the receiver is configured to receive the third radio waves from the first bridge and the fourth radio waves from the second bridge.

6. The system of claim 4, wherein the smart device is located in a different room than the first incubation apparatus and the second incubation apparatus.

7. The system of claim 6, wherein the first incubation apparatus is located in a different room than the second incubation apparatus.

8. The system of claim 7, wherein the first bridge is located in a same room as the first incubation apparatus, and the second bridge is located in a same room as the second incubation apparatus.

9. The system of claim 1, wherein data communicated by the first radio waves and the second radio waves is based on a first short-range wireless technology standard, and data communicated by the third radio waves is based on a second short-range wireless technology standard.

10. The system of claim 1, further comprising:
 a third pH apparatus within a third incubation chamber of the first incubation apparatus; and
 a fourth pH apparatus within a fourth incubation chamber of the second incubation apparatus.

11. The system of claim 1, wherein embryo culture dishes are in at least some of the two or more incubation chambers of the two or more incubation apparatuses, and the first pH apparatus and the second pH apparatus are detached from the separate embryo culture dishes.

* * * * *